United States Patent
Shodai et al.

(10) Patent No.: US 6,858,230 B1
(45) Date of Patent: Feb. 22, 2005

(54) PROCESS FOR PRODUCING MEDICINAL COMPOSITION OF BASIC HYDROPHOBIC MEDICINAL COMPOUND

(75) Inventors: Hidekazu Shodai, Amagasaki (JP); Noboru Nagafuji, Sakai (JP); Shuichi Matsuda, Amagasaki (JP); Yusuke Suzuki, Settsu (JP)

(73) Assignee: Shionogi & Co., Ltd., Osaka (JP)

( * ) Notice: Subject to any disclaimer, the term of this patent is extended or adjusted under 35 U.S.C. 154(b) by 0 days.

(21) Appl. No.: 09/958,549

(22) PCT Filed: Apr. 6, 2000

(86) PCT No.: PCT/JP00/02213

§ 371 (c)(1),
(2), (4) Date: Oct. 11, 2001

(87) PCT Pub. No.: WO00/61109

PCT Pub. Date: Oct. 19, 2000

(30) Foreign Application Priority Data

Apr. 12, 1999 (JP) ............................................ 11-104041

(51) Int. Cl.[7] ........................... A61K 9/14; A61K 9/127; A61K 9/20
(52) U.S. Cl. ........................ 424/489; 424/450; 424/464
(58) Field of Search ................................ 424/489, 464, 424/450

(56) References Cited

U.S. PATENT DOCUMENTS

| | | | |
|---|---|---|---|
| 5,442,048 A | * 8/1995 | Meister et al. | 536/20 |
| 5,534,502 A | * 7/1996 | Seki et al. | 514/31 |
| 5,716,642 A | 2/1998 | Bagchi et al. | 424/489 |
| 5,762,992 A | * 6/1998 | Takeuchi et al. | 426/548 |
| 5,910,506 A | 6/1999 | Sugimoto et al. | 514/397 |
| 6,147,097 A | 11/2000 | Sugimoto et al. | 514/341 |

FOREIGN PATENT DOCUMENTS

| | | |
|---|---|---|
| EP | 0 382 150 | 8/1990 |
| JP | 63-20302 | 1/1988 |
| JP | 363027501 A * | 2/1988 |
| JP | 63-210101 | 8/1988 |
| WO | 87/07618 | 12/1987 |

* cited by examiner

Primary Examiner—Shelley A. Dodson
(74) Attorney, Agent, or Firm—Wenderoth, Lind & Ponack, L.L.P.

(57) ABSTRACT

The present invention provides a method for preparation of a pharmaceutical composition which comprises suspending a hydrophobic medical compound without generating foams.

The present inventors have directed attention to properties of a hydrophobic medical compound and found a method for preparation of a pharmaceutical composition which comprises suspending and dispersing a basic hydrophobic medical compound, and neutralizing with a basic aqueous solution.

10 Claims, 4 Drawing Sheets

PROCESS FOR PRODUCING MEDICINAL COMPOSITION OF BASIC HYDROPHOBIC MEDICINAL COMPOUND

This application is a 371 of PCT/JP00/02213 filed Apr. 6, 2000.

TECHNICAL FIELD

This invention relates to a method for preparation of a pharmaceutical composition comprising a basic hydrophobic medical compound.

BACKGROUND ART

In preparation of pharmaceutical compositions, a spray dry method is often used. Japanese Patent Publication Kokai 1988-20302 discloses a spray dry method which comprises spraying an acidic solution of chitosan. Japanese Patent Publication Kokai 1988-210101 discloses a method which comprises spraying an acidic solution of chitosan followed by neutralization with a basic solution. These methods are used for reducing or adjusting the particle size of chitosan and characterized in using an acidic solution of chitosan. These documents do not disclose or indicate the utility and dispersion of a suspension.

In preparation of pharmaceutical compositions comprising a hydrophobic medical compounds, an aqueous suspension must be prepared when a spray dry method is used. The preparation of the above suspension is often difficult because a direct addition of the hydrophobic compound to water generates micro foams to form a foaming layer. The foaming layer is not easily degassed due to its stability.

As a method for suspending a hydrophobic medical compound without generating foams, the following methods are known; (1) a method for suspending under reduced pressure, and (2) a method using organic solvents.

The above method (1) requires special equipment. The above method (2) is accompanied with problems such as the danger of explosion and the residual solvents.

DISCLOSURE OF INVENTION

The present invention provides a method for preparation of a pharmaceutical composition, which comprises suspending a hydrophobic medical compound without forming foams. The present method does not require any special equipment and excludes the conventional problems relating to the danger of explosion and the residual solvents.

The present inventors have researched for developing a method for preparation of a pharmaceutical composition, which is characterized by suspending and dispersing a hydrophobic medical compound without forming foams, and have found that when a hydrophobic medical compound is basic, the formation of foams can be suppressed by the suspending and dispersing the compound in an acidic solution, whereby usual methods for stirring can be used for suspending and dispersing.

The present inventors have further found that the above obtained acidic suspension of a basic hydrophobic medical compound does not form a foaming layer even upon neutralization with a basic aqueous solution. The obtained suspension is neutral and so can be used for preparation of pharmaceutical compositions such as granulation process without rusting pharmaceutical equipment.

Thus, in the present invention, the generation of micro foams and formation of a foaming layer, which occur in the direct addition of a basic hydrophobic medical compound to water (e.g., purified water), can be suppressed by suspending and dispersing the basic hydrophobic medical compound in an acidic solution, followed by neutralization with a basic aqueous solution.

A spray dry method which comprises spraying and drying a suspension of a compound in atmosphere at high temperature to prepare a dried granule, requires preparation of a suspension of which the suspensibility and dispersibility is improved. The suspension of the present invention, therefore, is useful.

This present invention provides:
1) a method for preparation of a pharmaceutical composition which comprises a process of suspending and dispersing a basic hydrophobic medical compound in an acidic aqueous solution and a process of neutralizing the suspension obtained through said suspending and dispersing process with a basic aqueous solution,
2) a method for preparation of a pharmaceutical composition which comprises a process of suspending and dispersing a basic hydrophobic medical compound in an acidic aqueous solution, a process of neutralizing the suspension obtained through said suspending and dispersing process with a basic aqueous solution, and a process of spraying and drying the suspension neutralized through said neutralizing process in atmosphere at high temperature,
3) the method for preparation of a pharmaceutical composition according to the above 1) or 2) which is carried out for the purpose of suppressing a formation of a foaming layer,
4) the method for preparation of a pharmaceutical composition according to the above 1) or 2) which is carried out for the purpose of improving the suspensibility and dispersibility,
5) the method for preparation of a pharmaceutical composition according to any one of the above 1) to 4) wherein the acidic aqueous solution is an aqueous solution of malic acid, citric acid or phosphoric acid,
6) the method for preparation of a pharmaceutical composition according to any one of the above 1) to 5) wherein the basic aqueous solution is an aqueous solution of sodium hydroxide or potassium hydroxide,
7) the method for preparation of a pharmaceutical composition according to any one of the above 1) to 6) wherein the basic hydrophobic medical compound is a pyridine derivative, an imidazole derivative or an alkylamine derivative,
8) the method for preparation of a pharmaceutical composition according to any one of the above 1) to 7) wherein the basic hydrophobic medical compound is 5-(3,5-dichlorophenyl)thio-4-isopropyl-1-(4-pyridyl)methyl-1H-imidazol-2-ylmethyl carbamate,
9) the method for preparation of a pharmaceutical composition according to any one of the above 1) to 8) wherein the pharmaceutical composition is an suspension, a dry granule, a tablet or a dry syrup, and
10) a pharmaceutical composition which is prepared by a method according to any one of the above 1) to 9).

BEST MODE FOR CARRYING OUT THE INVENTION

Figure 1:
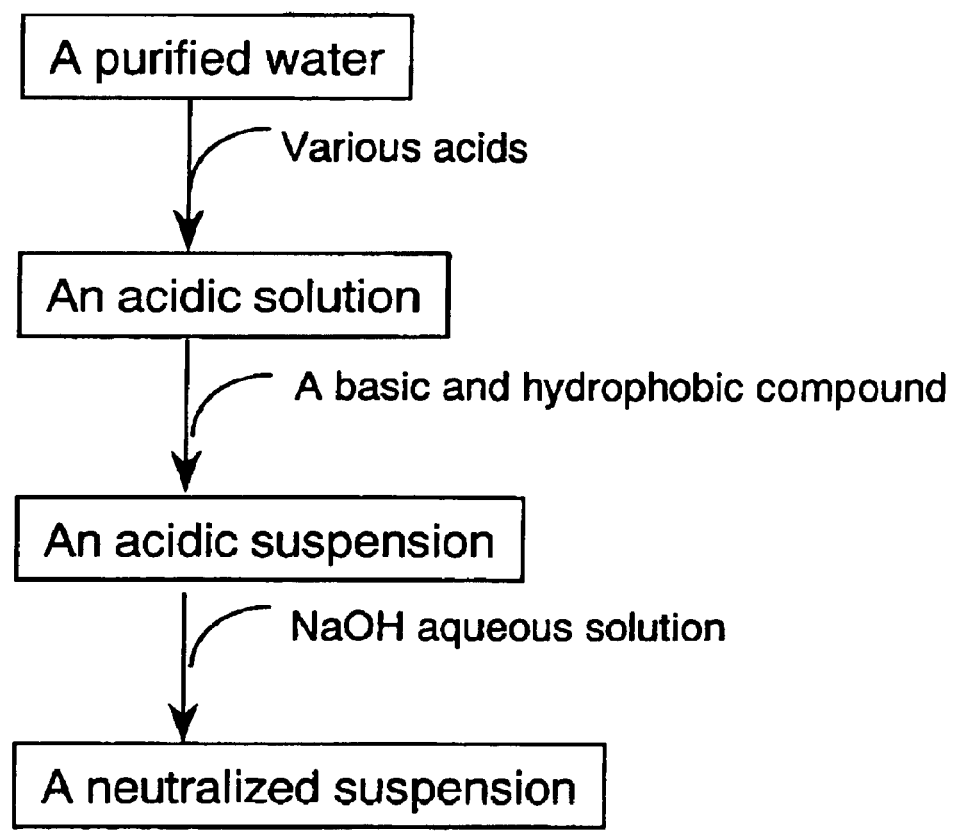
FIG. 1 shows an example of the step of the present invention.

The present invention provides a method for preparation of a pharmaceutical composition which comprises a process of suspending and dispersing a basic hydrophobic medical compound in an acidic aqueous solution, a process of neutralizing the obtained suspension with a basic aqueous solution, and a process of spraying and drying the obtained suspension in atmosphere at high temperature. For example, the present invention includes the following steps, some of which are shown in FIG. 1.

(A) An acidic solution is prepared by adding various acids to water such as purified water.

(B) A basic hydrophobic medical compound is added and dispersed in an acidic solution obtained in the above (A).

(C) A suspension is prepared by neutralizing the suspension obtained in the above (B) with a basic solution.

(D) A dried granule is prepared by spraying and drying the suspension obtained in the above (C) in atmosphere at high temperature.

(E) A pharmaceutical composition is prepared by mixing the dried granule obtained in the above (D) with various excipients.

In the procedure (A), an acid may be added to water, and vice versa.

A acid to be used in the present invention includes a generally used acid such as an organic acid (e.g, malic acid, citric acid, lactic acid, acetic acid or the like) or an inorganic acid (e.g., hydrochloric acid, phosphoric acid or the like). Preferred is malic acid, citric acid, phosphoric acid or the like.

In order to dissolve a basic hydrophobic medical compound in water, one mole equivalent of an acid to the compound is generally required to form a salt. In the present invention, an acidic aqueous solution is used for improving the suspensibility and dispersibility, not for dissolving a basic hydrophobic compound. Therefore, the amount of an acid in an acidic aqueous solution is 0.01 to 0.5 mole equivalent, preferably 0.04 to 0.2 mole equivalent to a basic hydrophobic medical compound.

In the procedure (B), a basic hydrophobic medical compound is added to an acidic solution obtained in the procedure (A), whereby preventing a suspension from forming a foaming layer, which is formed when a compound is added to a neutral solution, and giving a suspension with a high dispersibility. The control of the amount of an acid in the procedure (A) can well lead to the preparation of a suspension, not a solution.

A basic hydrophobic medical compound in the present invention includes a hydrophobic organic compound exhibiting basicity and having a pharmaceutical activity, and preferred is pyridine derivatives, imidazole derivatives or alkylamine derivatives. Pyridine derivatives include hydrophobic organic compounds having a pyridine ring. Imidazole derivatives include hydrophobic organic compounds having an imidazole ring. Preferred are hydrophobic organic compounds having an imidazole ring and a pyridine ring. Alkylamine derivatives include hydrophobic organic compounds having an alkylamino group.

Examples of imidazole derivatives include a compound of the formula (I):

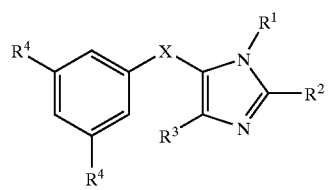

wherein $R^1$ is alkyl, optionally substituted aralkyl or optionally substituted heteroaralkyl, $R^2$ is carbamoyloxyalkyl, hydroxyalkyl, aminoalkyl, acetoxyalkyl or cyanoalkyl, $R^3$ is ethyl or isopropyl, $R^4$ is alkyl or halogen, and X is —S— or —CH$_2$—. These compounds are useful as anti HIV agents and disclosed in WO96/10019.

Alkyl includes $C_1$–$C_4$ straight or branched alkyl, for example, methyl, ethyl, n-propyl, isopropyl, n-butyl, isobutyl, sec-butyl or tert-butyl.

Aralkyl includes the above alkyl substituted with aryl such as phenyl, naphthyl or the like, for example, benzyl, phenethyl, phenylpropyl, naphthylmethyl, naphthylethyl or the like.

Heteroaralkyl includes the above alkyl substituted with heteroaryl such as pyridyl, for example, picolyl, pyridylethyl, pyridylpropyl or the like.

Carbamoyloxyalkyl, hydroxyalkyl, aminoalkyl, acetoxyalkyl and cyanoalkyl includes the above alkyl substituted with carbamoyloxy, hydroxy, amino, acetoxy and cyano, respectively, for examples, carbamoyloxymethyl, carbamoyloxyethyl, carbamoyloxypropyl, hydroxymethyl, hydroxyethyl, hydroxypropyl, aminomethyl, acetoxymethyl, cyanomethyl, cyanoethyl or the like. Preferred is carbamoyloxymethyl, hydroxymethyl or aminomethyl.

The compound of the formula (I) wherein $R^1$ is optionally substituted picolyl belongs to imidazole derivatives as well as pyridine derivatives. The examples include compound (I-1), 5-(3,5-dichlorophenyl)thio-4-isopropyl-1-(4-pyridyl) methyl-1H-imidazol-0.2-ylmethyl carbamate or the like.

Examples of pyridine derivatives include nicotinamide, nikethamide, isoniazid, nialamide, ethionamide, prothionamide or the like.

Examples of alkyl amine derivatives include pindolol, noscapine or the like.

The structures of these compounds are shown below.

Compound (I-1)

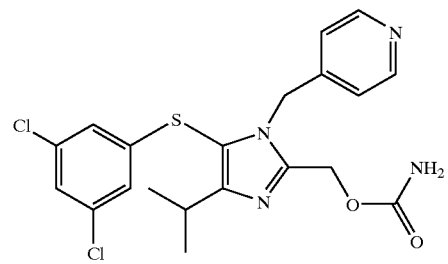

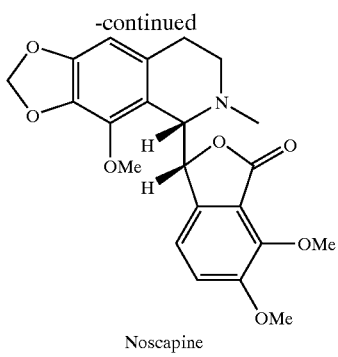

Noscapine

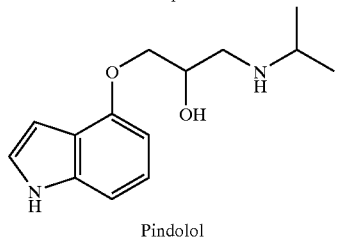

Pindolol

In the procedure (C), the rusty of equipment can be prevented by neutralizing the suspension obtained in (B) with a basic aqueous solution. Though thus obtained suspension does not form a foaming layer even under stirring in spite of the neutrality. The present invention, therefore, can provide a suspension exhibiting the high suspensibility and dispersibility.

A basic solution includes a solution in which a general base is dissolved. A base includes, for example, sodium hydroxide, potassium hydroxide, sodium hydrogencarbonate or the like. Preferred is sodium hydroxide or potassium hydroxide.

In the step (D), a dried granule can be prepared. A generally known spray dry method and equipment can be used.

In the step (E), various pharmaceutical compositions such as a tablet, a dry syrup or the like can be prepared. The pharmaceutical composition may include excipients, because the present invention is characterized by the above steps (A) to (E).

A pharmaceutical composition includes a preparing composition and a prepared composition, for example, a suspension, a granule, a tablet, a capsule, a dry syrup (e.g, pediatric dry syrup) or the like. The pharmaceutical composition of the present invention includes an suspension obtained in (C) and a granule obtained in (D) as well as a tablet, a capsule, a dry syrup or the like prepared by using them. A pharmaceutical composition (e.g, a tablet, a dry syrup (e.g, pediatric dry syrup)) prepared through the present invention exhibits improvement of dissolution rate, suspendabitily, dispersibility and stability, as compared with a pharmaceutical composition prepared through direct addition of a hydrophobic compound to water.

As described above, a spray dry method can not be used because of forming a foaming layer when a compound is basic and hydrophobic. The present invention enables a pharmaceutical composition to be prepared through a spray dry method even when a compound is basic and hydrophobic. A pharmaceutical composition (e.g., a tablet, a dry syrup) prepared through the present invention exhibits improvement of bioavailability, as compared with a pharmaceutical composition prepared without using a spray dry method (e.g., a pharmaceutical composition prepared through a general granulation method).

Figure 2:
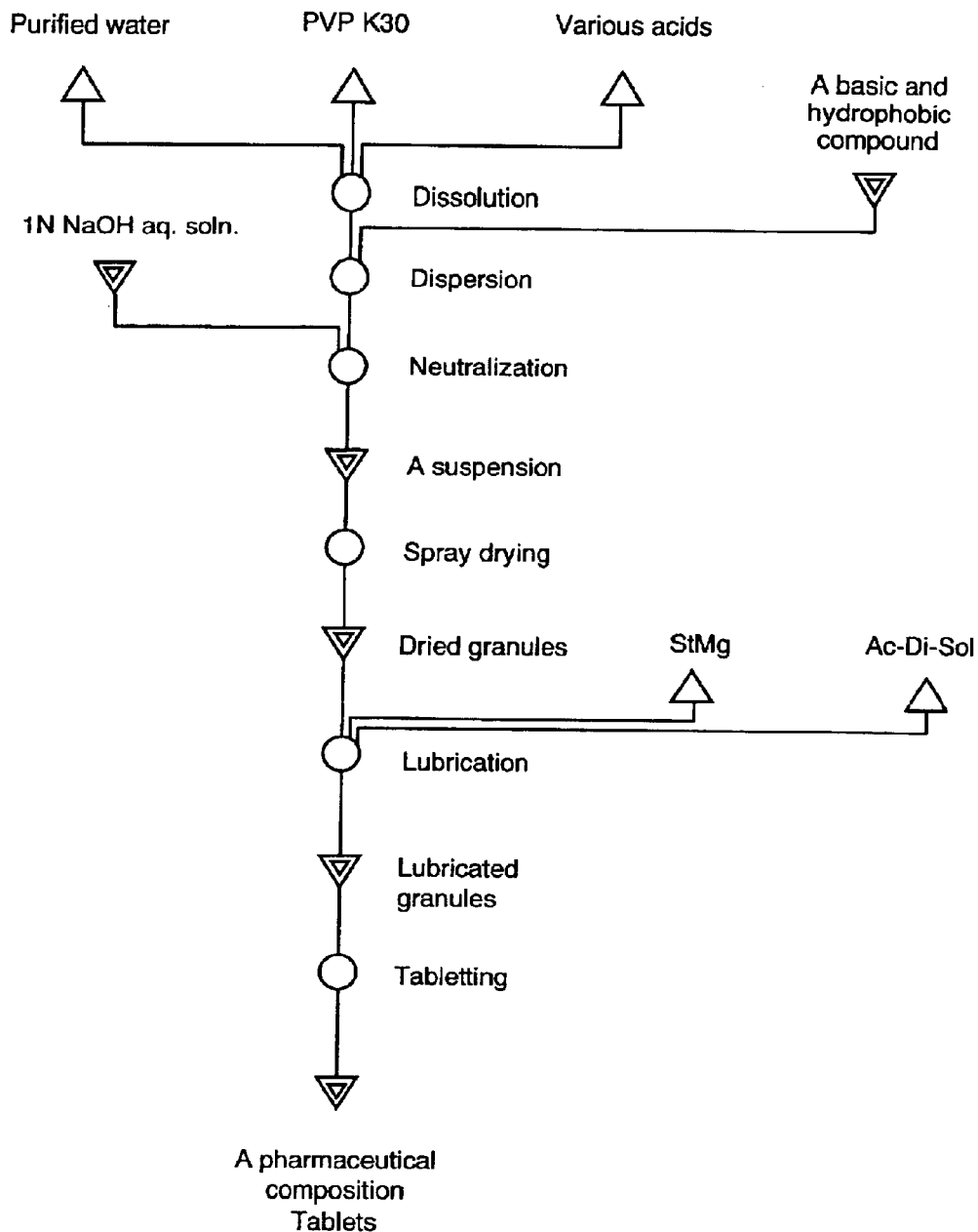
FIG. 2 shows an example of the step of the present invention for manufacturing tablets.
Figure 3:
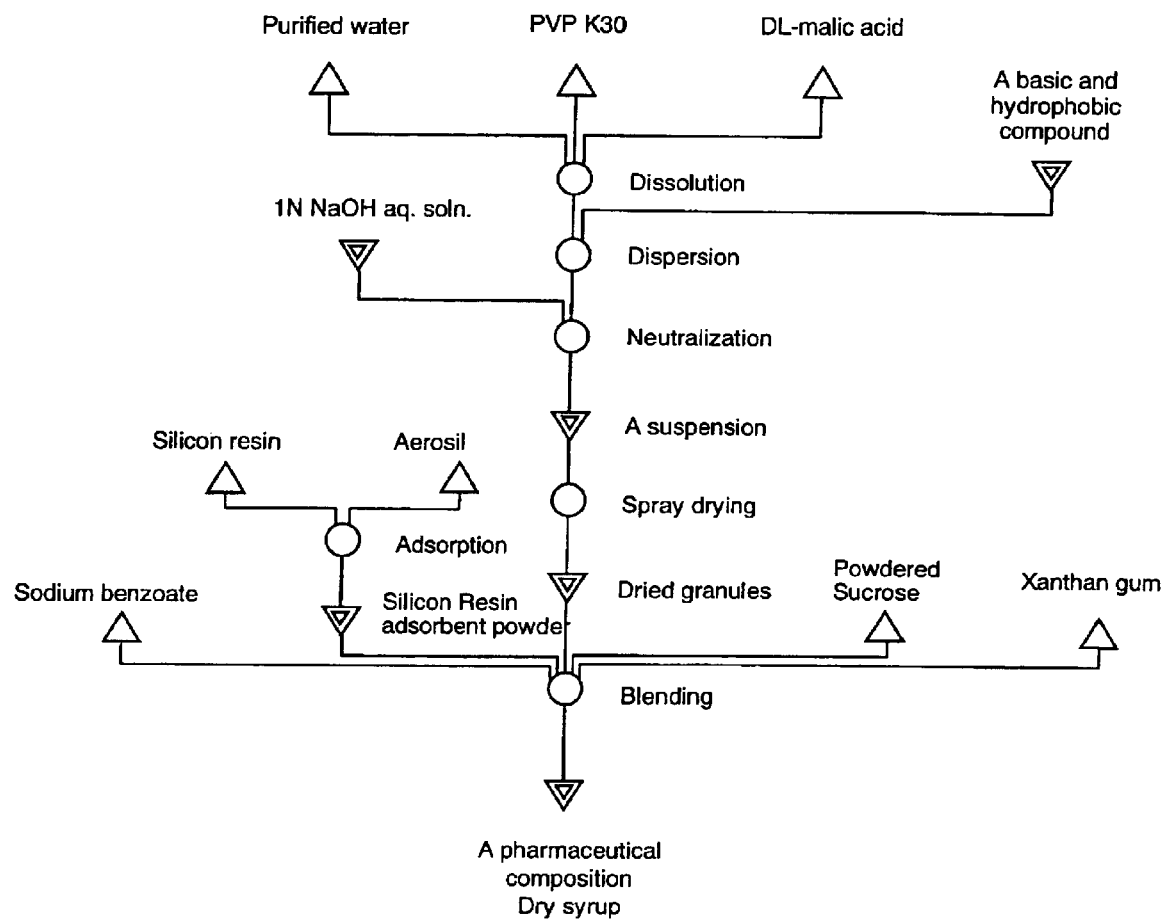
FIG. 3 shows an example of the step of the present invention for manufacturing a pediatric dry syrup.

The steps of a tablet and a dry syrup (a pediatric dry syrup) are shown in FIGS. 2 and 3, respectively. The terms to be used in Figure show the following meanings. (PVP K30: polyvinylpyrrolidone K30, Ac-Di-Sol: Crosscarmellose Sodium, Aerosil: light anhydrous silicic acid).

FIG. 2 shows a flowchart for tablet manufacturing. To a solution containing purified water, various acids and PVP K30 was added and suspended a basic hydrophobic medical compound. Second, a suspension was prepared by neutralizing the above suspension with a NaOH aqueous solution. A dried granule was prepared by spraying and drying the suspension. A lubricated granule was prepared by adding StMg and Ac-Di-Sol thereto. A tablet was prepared by tableting the above obtained lubricated granule.

FIG. 3 shows a flowchart for dry syrup manufacturing. To a solution containing purified water, malic acid and PVP K30 was added and suspended a basic hydrophobic medical compound. Second, a suspension was prepared by neutralizing the above suspension with a NaOH aqueous solution. A dry granule was prepared by spraying and drying the suspension. A dry syrup was prepared by mixing the above dried granule with a silicon resin adsorbent powder prepared from aerosil and silicon resin, sodium benzoate, powdered sucrose and xanthan gum.

PVP K30 is used as a binder. A binder is not limited to PVP K30. Any water-soluble binder, for example, HPC, Dextrin can be used.

Ac-Di-Sol is used as a disintegrator. Any disintegrator, for example, LHPC, CMC-Ca, can be used.

StMg is used as a lubricant. Xanthan gum is used as a thickener. Aerosil is used as an absorbent. Silicon resin is used as a defoaming agent and a suspending agent. Powdered sugar is used as a sweetener and a flavoring agent. Each agent is not limited thereto.

EXAMPLE

Examples of the present invention are shown below. An acidic solution to be used in the following examples is a solution of malic acid, citric acid and phosphoric acid. A basic aqueous solution to be used in the following examples is a solution of NaOH. A basic hydrophobic compound to be used in the following examples is compound (I-1), pindolol and noscapine. The compound (I-1) is 5-(3,5-dichlorophenyl)thio-4-isopropyl-1-(4-pyridyl)methyl-1H-imidazol-2-ylmethyl carbamate.

Example 1

A Method for Preparation of a Tablet of Compound (I-1)

100 g of PVP K30 was dissolved to 1600 g of purified water. These aqueous solution were acidified by DL-Malic acid. The compound (I-1) was dispersed in the acidic solution under stirring. The suspension was neutralized with 230 g of 13% NaOH aqueous solution.

A dried granule was prepared by spraying and drying the obtained suspension with L-8 type of spray dryer. 700 g of the granule was blended with 21 g of Ac-Di-Sol and 28 g of StMg to give a lubricated granule. A tablet (weight: 631.3 mg, thickness: 5.0 mm per a tablet) was prepared by using rotary tabletting machine (LIBRA 836BK-AWCZ) equipped with couplet type of pestle (18.5×7.9 mm).

The contents of the obtained tablet were shown in Table 1.

TABLE 1

The contents of a tablet prepared by a spray dry method adding an acid.

| | Weight per a tablet |
|---|---|
| Compound (I-1) | 500.0 Mg |
| PVP K30 | 50.0 |
| DL-malic acid | 25.0 |
| Sodium hydroxide | 15.0 |
| StMg | 23.6 |
| Ac-Di-Sol | 17.7 |
| Total | 631.3 mg/T |

Example 2

A Method for Preparation of a Pediatric Dry Syrup of Compound (I-1)

100 g of PVP K30 was dissolved to 1600 g of purified water. These aqueous solution were acidified by DL-Malic acid. The compound (I-1) was dispersed in the acidic solution under stirring. The suspension was neutralized with 230 g of 13% NaOH aqueous solution.

A dried granule was prepared by spraying and drying the obtained suspension with L-8 type of spray dryer. 236 g of the granule was blended with 743 g of powdered sugar, 15 g of xanthan gum, 4 g of sodium benzoate, and 2 g of a silicon resin adsorbent powder to give a pediatric dry syrup.

The contents of the obtained pediatric dry syrup were shown in Table 2.

TABLE 2

The contents of a dry syrup by a spray dry method adding an acid.

| Compound (I-1) | 200.0 Mg |
|---|---|
| PVP K30 | 20.0 |
| DL-malic acid | 10.0 |
| Sodium hydroxide | 6.0 |
| Powdered sugar | 743.0 |
| Xanthan gum | 15.0 |
| Sodium benzoate | 4.0 |
| Silicon resin | 1.0 |
| Aerosil | 1.0 |
| Total | 1000.0 Mg |

Example 3

A Method for Preparation of a Suspension of the Compound (I-1)

Example 3-1

Adding Malic Acid 50 g of PVP K30 was dissolved to 800 g of purified water. These aqueous solution were acidified by DL-Malic acid. The compound (I-1) was suspended in the acidic solution under stirring. The suspension was neutralized with 115 g of 13% NaOH aqueous solution to give a suspension.

Example 3-2

Adding Citric Acid

In place of malic acid in Example 3-1, citric acid was used.

Example 3-3

Adding Phosphoric Acid

In place of malic acid in Example 3-1, phosphoric acid was used.

Reference Example 3-4

Adding No Acid

No acid was used.

Example 4

A Method for Preparation of a Suspension of Pindolol

In place of the compound (I-1) in Example 3-1, pindolol was used.

Example 5

A Method for Preparation of a Suspension of Noscapine

In place of the compound (I-1) in Example 3-1, noscapine was used.

Experiment 1 (Dissolution Profile)

Figure 4:
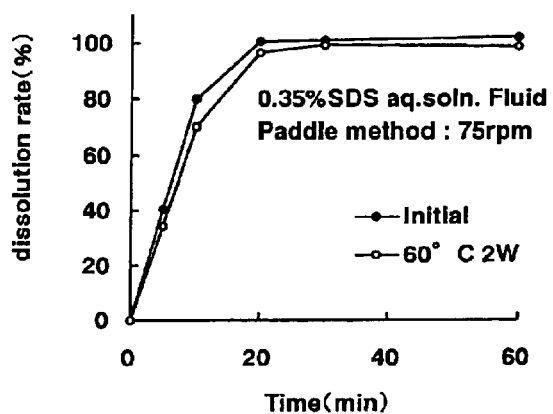
FIG. 4 shows dissolution profile of a pharmaceutical composition of the present invention.
Figure 4:
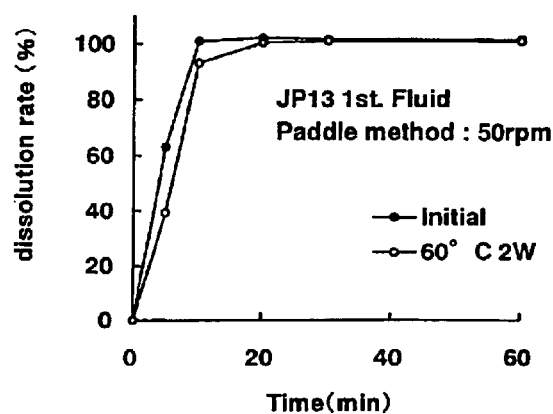

Dissolution profile of the tablet of the compound (I-1) obtained in Example 1 was examined. The tablet obtained in Example 1 was contained in a glass bottle and stored at 60° C. for two weeks under sealing. The obtained sample was examined by dissolution test in Japanese pharmacopeia. The results were shown in FIG. 4.

Experiment 2 (Content/Appearance)

Content and appearance of a tablet of the compound (I-1) obtained in Example 1 were examined. The tablet obtained in Example 1 was contained in a glass bottle and stored at 60° C. for two weeks under sealing. The tablet obtained in Example 1 was put on a glass schale and irradiated by light of 3570Lx for 168 hours (energy of irradiation: 600,000Lx/h). Each tablet was examined in content? test in Japanese pharmacopeia. Stability of appearance was measured by color analyzer (TC-180MK II, Tokyo Electrics) and compared with that before treatment.

The results were shown in Table 3.

TABLE 3

Remaining rate of active ingredient/change of appearance

| Condition | Remaining rate | Change of appearance (ΔE) |
|---|---|---|
| 60° C., 2 weeks, glass bottle | 101.4 | 0.73 |
| Irradiation (600,000 Lx/hr) | 100.0 | 2.55 |

Experiment 3 (Physical Stability)

Physical stability of the pediatric dry syrup of the compound (I-1) obtained in Example 2 was examined. 1000 mg of the dry syrup obtained in Example 2 was contained in 50 cc of centrifugation tube and mixed with 50 ml of purified water and lightly shaken. Dispersion of the granule was observed by the naked eye. A dispersed suspension was stored at room temperature for 2 days and shaken again. Dispersion of the granule was observed by the naked eye.

The results were shown in Table 4.

TABLE 4

| Physical stability | |
|---|---|
| Dispersibility and suspensibility | Good |
| Re-dispersibility (After 2 days) | Good |
| Change of appearance (After 2 weeks at 60° C.) | None |

Experiment 4 (Dispersibility of Active Ingredient in an Acidic Suspension Including Various Kinds of Acids)

Dispersibility of the compound (I-1) in an acidic suspension obtained in Example 3-1 to 3-4 including various kinds of acids was examined. Dispersibility was observed by the naked eyes at the time of preparation of an suspension.

The contents of a suspension and the results of the above experiment were shown in Table 5.

TABLE 5

The contents of a suspension and dispersibility of the compound (I-1) in a suspension including various kinds of acids.

| | malic acid | citric acid | Phosphoric acid | No acid |
|---|---|---|---|---|
| Compound (I-1) | 500 g | 500 G | 500 g | 500 g |
| PVP K30 | 50 | 50 | 50 | 50 |
| DL-malic acid | 25 | — | — | — |
| citric acid | — | 8 | — | — |
| Phosphoric acid | — | — | 4 | — |
| NaOH | 15 | 5 | 2.5 | — |
| Purified water | 800 | 800 | 800 | 800 |
| Total | 1390 g | 1363 G | 1356.5 g | 1350 g |
| Dispersibility of drug substance | Good | Good | Good | Formation of foams |

Experiment 5 (Dispersibility of a Basic Compound in a Suspension)

Dispersibility of active ingredient in the suspension obtained in Example 3-1, 4 and 5 was examined in accordance with Experiment 4.

The contents of the suspension and the results of Experimet were shown in Table 6.

TABLE 6

A suspension of a basic hydrophobic compound and dispersibility of drug substance

| | Compound (I-1) | Noscapine | Pindolol |
|---|---|---|---|
| Compound (I-1) | 500 g | — g | — g |
| Noscapine | — | 500 | — |
| Pindolol | — | — | 500 |
| PVP K30 | 50 | 50 | 50 |
| DL-malic acid | 25 | 25 | 25 |
| NaOH | 15 | 15 | 15 |
| Purified water | 800 | 800 | 800 |
| Total | 1390 g | 1390 g | 1390 g |
| Dispersibility of drug substance | Good | Good | Good |

INDUSTRIAL APPLICABILITY

The present invention enables a basic hydrophobic medical compound to be suspended without generating foams. A suspension, therefore, can be easily prepared. Since the suspension is neutral, the present invention prevents pharmaceutical equipment from getting rusty. A pharmaceutical composition prepared through the present invention is improved in dissolution rate, suspensibility, dispersibility, stability and bioavailability.

What is claimed is:

1. A method for preparation of a pharmaceutical composition, which comprises a process of suspending and dispersing a basic hydrophobic medical compound in an acidic aqueous solution, and a process of obtaining a neutral suspension by neutralizing the obtained suspension with a basic aqueous solution.

2. A method for preparation of a pharmaceutical composition, which comprises a process of suspending and dispersing a basic hydrophobic medical compound in an acidic aqueous solution, a process of obtaining a neutral suspension by neutralizing the obtained suspension with a basic aqueous solution, and a process of spraying and drying the suspension neutralized through said neutralizing process in an atmosphere at high temperature.

3. The method for preparation of a pharmaceutical composition according to claim 1 or 2 which is carried out for the purpose of suppressing a formation of a foaming layer.

4. The method for preparation of a pharmaceutical composition according to claim 1 or 2 which is carried out for the purpose of improving the suspensibility and dispersibility.

5. The method for preparation of a pharmaceutical composition according to any one of claims 1 or 2 wherein the acidic aqueous solution is an aqueous solution of malic acid, citric acid or phosphoric acid.

6. The method for preparation of a pharmaceutical composition according to any one of claims 1 or 2 wherein the basic aqueous solution is an aqueous solution of sodium hydroxide or potassium hydroxide.

7. The method for preparation of a pharmaceutical composition according to any one of claims 1 or 2 wherein the basic hydrophobic medical compound is a pyridine derivative, an imidazole derivative or an alkylamine derivative.

8. The method for preparation of a pharmaceutical composition according to any one of claims 1 or 2 wherein the basic hydrophobic medical compound is 5-(3,5-dichlorophenyl)thio-4-isopropyl-1-(4-pyridyl)methyl-1H-imidazol-2-ylmethyl carbamate.

9. The method for preparation of a pharmaceutical composition according to any one of claims 1 or 2 wherein the pharmaceutical composition is a suspension, a dry granule, a tablet or a dry syrup.

10. A pharmaceutical composition which is prepared by a method according to any one of claims 1 or 2.

* * * * *